United States Patent [19]

Purdy

[11] Patent Number: 5,263,964
[45] Date of Patent: Nov. 23, 1993

[54] COAXIAL TRACTION DETACHMENT APPARATUS AND METHOD

[75] Inventor: Phillip D. Purdy, Dallas, Tex.
[73] Assignee: Coil Partners Ltd., Dallas, Tex.
[21] Appl. No.: 879,839
[22] Filed: May 6, 1992
[51] Int. Cl.$^5$ .............................................. A61B 17/00
[52] U.S. Cl. .................................... 606/200; 128/899
[58] Field of Search ............... 606/191, 194, 195, 198, 606/200; 623/1, 12; 604/104–105; 128/899

[56] References Cited

U.S. PATENT DOCUMENTS

| | | |
|---|---|---|
| 3,868,956 | 3/1975 | Alfidi et al. |
| 4,365,632 | 12/1982 | Kortum |
| 4,425,908 | 1/1984 | Simon |
| 4,494,531 | 1/1985 | Gianturco |
| 4,512,338 | 4/1985 | Balko et al. |
| 4,638,803 | 1/1987 | Rand |
| 4,832,055 | 5/1989 | Palestrant ........................... 128/899 |
| 4,957,501 | 9/1990 | Lahille et al. |
| 4,994,069 | 2/1991 | Ritchart et al. |
| 5,071,407 | 12/1991 | Termin et al. |

Primary Examiner—Stephen C. Pellegrino
Assistant Examiner—William W. Lewis
Attorney, Agent, or Firm—Hubbard, Thurman, Tucker & Harris

[57] ABSTRACT

The present coaxial traction detachment system improves intravascular occlusion by providing a means for greater control in the placement of endovascular devices. The detachment apparatus (10) includes a guide wire (16) slidably disposed within a sheath (14). An endovascular device (18) is attached to the distal end of the guide wire (16). The sheath (14) is guided through a catheter (12) to a device detachment location. The device (18) is attached to the wire (16) either by a glue or solder or by mechanical means such as the intertwining of the device (18) to the guide wire (16). Following device placement and prior to detachment, the operator is able to observe the position and configuration of the device. If the position is unsatisfactory, he need only withdraw the sheath to remove the device. If placement is satisfactory, the system utilizes a coaxial detachment method such that the operator places traction on the guide wire and the device is pulled against the outer sheath, causing it to detach.

17 Claims, 2 Drawing Sheets

COAXIAL TRACTION DETACHMENT APPARATUS AND METHOD

TECHNICAL FIELD OF THE INVENTION

This invention relates to a coaxial traction detachment apparatus and method for placement of devices within blood vessels for the purpose of permanent occupancy at a controlled location in the blood vessel by the device. The most frequent current use of such devices is vaso-occlusion by metallic coils delivered through a catheter to the site of occlusion.

BACKGROUND OF THE INVENTION

Endovascular use of devices to occlude blood vessels has become widespread both geographically around the world and anatomically throughout the body. In endovascular therapy, the doctor attempts to produce blockage or occlusion of blood flow through a vessel in order to stop bleeding. The vessel may be either an artery or a vein. His goal may be to prevent the vessel from hemorrhaging, to limit bleeding during surgery, or to stop an abnormal blood flow pattern between blood vessels (i.e. fistulas). Devices can also be used to prevent growth of abnormal protrusions from blood vessels, such as aneurysms, by creating an occlusion within the aneurysm. This occlusion minimizes or eliminates the blood pulsations which cause abnormal stresses on the wall of the aneurysm.

Several endovascular devices have been created to accomplish these goals. These devices include "glue," thrombosis producing particles, balloons, and coils. Central to the success of the device is its ability to be precisely placed within the vessel and its ability to adhere to the vessel wall. Placement typically occurs through a catheter from a proximal position outside of a patient to a distal position within the patient. Each type of device has particular attributes and particular drawbacks in its efficacy and its ability to be placed.

"Glue" refers to a group of compounds that are injected into a vessel. The glue solidifies on the vessel wall. Solidification typically occurs due to exposure of the glue to electrolytes in the blood. Therefore, glue is not actually a "device" which is solid at the time of its introduction. Control of the placement of the glue is hampered due to the variability of its cure rate within the blood stream.

Thrombosis producing particles ca also be introduced into the vessel to produce blockage of that vessel. These particles can be formed of various material such as polyvinyl alcohol, silicone polymer, protein particles, glass beads, latex beads, or silk suture material. That blockage may be temporary or permanent, depending on whether and to what degree the particle is broken down in the body, resulting in recanalization of a blood vessel after occlusion. In the case of particles, blockage occurs at the point where the blood vessel diameter is smaller than the particle. Thus, if a small particle is released into a large vessel, the blood flow will carry the particle to the point where the vessel diameter diminishes to that of the particle. This is used to advantage in tumor or vascular malformation embolization, but has the disadvantage of loss of control over the point of occlusion.

A balloon can be introduced within the vessel by a catheter and then inflated within the blood vessel to produce occlusion. The balloon may be permanently attached to the catheter, or it can have a valve at the point of attachment which closes when the catheter is withdrawn, detaching the balloon in position without producing subsequent deflation With balloons permanently attached to a catheter, the blockage generally occurs at the point of placement of the tip of the catheter, such that the level of blockage is limited to the position of the tip of the catheter. That may be far into a vascular system, such as the brain, depending on the flexibility of the catheter and the skill of the operator, but the point of the occlusion is the tip of the catheter.

With detachable balloons, the method of detachment is usually traction of the balloon against the blood vessel, producing friction which causes resistance to withdrawal as the catheter is pulled out. Alternatively, balloons can also be detached by a so-called coaxial detachment system wherein detachment occurs by advancement of a larger catheter over a smaller catheter containing the balloon. The larger catheter contacts the inflated balloon preventing the withdrawal of the balloon. This permits the inner catheter to be removed from the balloon while the balloon maintains its position. However, this system is limited to larger vessels because the stiffness of both the outer and inner catheters limits their ability to advance into ever more tortuous, distal vessel portions.

Balloon occlusion devices can sometimes deflate or can even rupture the artery in which they are introduced, thus being somewhat hazardous and unpredictable. Also, balloon devices limit embolization options by producing vascular occlusion at the time of introduction. Thus, if combined embolization is desired using both particles and a more proximal occlusive device such as a balloon, the use of the balloon precludes the first use of the particles. Thus, balloons have the advantage of control over the point of occlusion but the inability to perform combined embolization while particles have the disadvantage of a lack of control over the point of occlusion.

A more recent endovascular device for small vessels, "coils," have been used for many years to present a solution to these problems in larger vessels. A coil is typically a stainless steel wire device wound such that its outer diameter matches the inner diameter of an angiographic catheter. The coil can be introduced into a catheter in a straight configuration and pushed through the catheter with a guide wire. As it exits the catheter, it can wind itself into a "coil" type configuration. The coil produces an obstacle in the blood vessel, causing blood to clot thereon. The clot blocks the blood vessel. Further development resulted in the addition of fibers of cotton or other material within the coil, increasing its propensity to cause thrombosis more quickly.

In recent years, advancements in catheter technology have allowed progressively more distal catheterizations. However, with more distal catheterizations, the stiffness of the stainless steel coil is a limitation. In response, small-diameter platinum "microcoils" were developed. These microcoils can be introduced through the catheter with a guide wire or, alternatively, be pushed by the force of an injection of water through the catheter, thus "injecting" them into the blood vessel. Some of these "coils" are actually straight, thus enabling them to follow flow in the vessel and act more like a particle. Some are curved, thus increasing the likelihood that they will not advance beyond the point of introduction. Still, all traditional coils have the disadvantage of a lack of control, insofar as they are free objects once they are introduced into the catheter. If the coils leave the catheter tip flowing in an untoward direction or if the catheter tip moves at the time of introduction, the physician has no control over this undesirable situation or ability to recall or reposition the coil. Thus, their successful placement is extremely dependent on the skills of the surgeon/radiologist placing them.

Recently, the Guglielmi Detachable Coil ("GDC coil") by Target Therapeutics has been introduced to address lack of placement control in a limited set of circumstances. The GDC coil is attached to a guide wire by way of a solder. The guide wire is threaded through the catheter, thus allowing the operator to assure placement in a desirable location prior to detachment. When detachment is desired, a low-voltage electric current is applied to the wire, resulting in electrolytic dissolution of the solder and detachment of the coil. This is the first commercial detachable coil and is currently undergoing FDA trials.

However, the GDC coil's detachment mechanism presents several disadvantages. First, it requires the electrolytic dissolution of solder. Long-term effects of this process are unknown. Second, the process of electrolysis is time-consuming, yet treatment of aneurysms or other diseases can require placement of multiple coils. Thus, while supposedly requiring only a few minutes, as more coils are placed, interactions between devices can take place which dissipate the electrolytic current and prolong detachment. Third, the diameter of the GDC coil is 0.010". This allows a shorter detachment time but limits the applicability of the device in many parts of the body and increases the number of coils needed to achieve results. If larger coils are used, more solder would be required and presumably longer detachments would ensue. The use of 0.010" coils means the use of 0.010" catheters instead of the more widely-used 0.018" catheters in the brain and 0.038" inner diameter catheters in other parts of the body. This size restriction constrains particle sizes for introduction of other particles and limits applications to smaller vessels and pathologies.

Therefore, a need exists for a more widely applicable detachment method. This detachment method should allow utilization of larger catheters and potentially allow utilization o stainless steel coils in many parts of the body under more controlled circumstances than have traditionally been employed. The detachment method should also provide the maximum placement control as well as the ability to withdraw the device prior to detachment. The detachment method should also allow the physician to observe and verify the location of the detached device. A need also exists for an apparatus incorporating such a detachment method. The development of a reliable device for intravascular detachment would not necessarily be limited in its applicability to coils, though that would be the most immediate application.

SUMMARY OF THE INVENTION

The present invention relates to a coaxial traction detachment apparatus and method which provides more precise and controlled placement of endovascular devices. The apparatus generally comprises a sheath flexible enough to negotiate its way through a tortuous catheter course Slidably disposed within the sheath is a guide wire. An endovascular device is attached to the distal end of the guide wire. The device can be unjacketed by and distal to the sheath. Alternatively, an endovascular device capable of a compressed or an uncompressed state can also be jacketed by the sheath.

The attachment between the device and the guide wire can be by either solid or mechanical means. Solid means can include the use of glue, solder or the like. Mechanical means can include an intermeshing of the device and the wire. In either case, the attachment point is the "weak link," and the force necessary to break this link is predetermined. If the device is unjacketed, the point of attachment between the device and the wire has a diameter larger than the sheath. If the device is jacketed, the point of attachment has a diameter less than the sheath.

The coaxial detachment method generally comprises placing the distal end of a catheter adjacent to a device detachment location within the patient. The sheath containing the guide wire is guided through the catheter until the distal end of the sheath is adjacent to the distal end of the catheter. The unjacketed device is then detached by placing traction on the guide wire. Alternatively, for jacketed devices capable of a compressed or an uncompressed state, the device is first advanced to an unjacketed position allowing the device to assume its uncompressed state. Then traction is placed on the wire, pulling the uncompressed device against the distal end of the sheath, thereby detaching it. The sheath and guide wire are typically made of tubular steel or polymer compounds which provide the appropriate stiffness to compression and flexibility to steer through vessels of a tortuous course.

The present method and apparatus retains the advantage of device retrievability if aberrant placement or catheter displacement occurs. In other words, until detachment, the coil may be withdrawn through the catheter. The present method also retains the option of applicability to stainless steel coils, larger platinum coils, or coils constructed of nonmetallic materials. The present invention can also be used for the placement of other devices, such as vena caval filters used for prevention of pulmonary emboli, for placement of intravascular stints, or for other solid intravascular devices in unforeseen applications. Also, the material used can allow observation and verification of placement prior to detachment by standard radiological means.

BRIEF DESCRIPTION OF THE DRAWINGS

For a more complete understanding of the present invention, and for further details and advantages thereof, reference is now made to the following Detailed Description taken in conjunction with the accompanying drawings, in which.

DETAILED DESCRIPTION OF THE INVENTION

Figure 1:
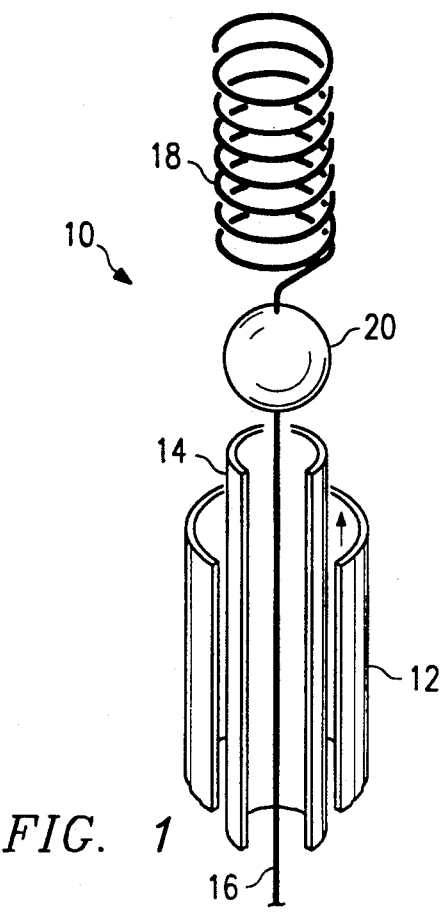
FIGS. 1 and 2 illustrate a first method of detaching an unjacketed endovascular device.
Figure 2:
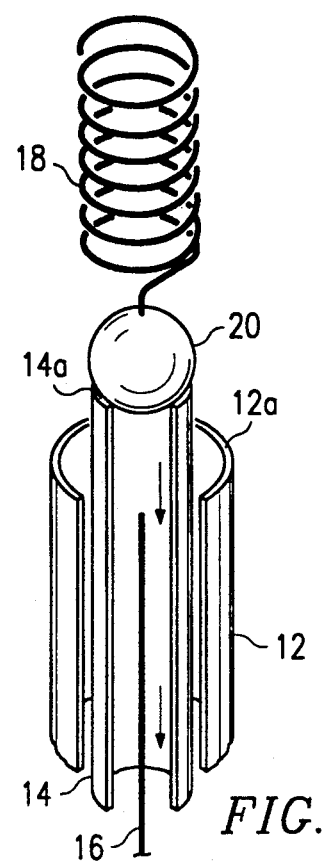

The present invention relates to a coaxial traction detachment apparatus and method which overcomes many of the disadvantages found in the prior art. Referring to FIGS. 1 and 2 simultaneously, a device 10 embodying the present system is disclosed. The device 10 comprises a sheath 14 within which a guide wire 16 is slidably disposed. The guide wire 16 has an endovascular device 18 attached to the distal end thereof at attachment point 20. The endovascular device 18 illustrated is a coil. The sheath 14 is slidably disposed within a sheath 14.

In practice, the distal end 12a of the catheter 12 is placed as close as possible to the desired device detachment location within the patient's body. The sheath 14 and guide wire 16 therein are then guided into the catheter 12 as a unit. In one embodiment, the wire 16 is jacketed within the sheath 14 while the device 18 is located distal to the sheath 14. The point of attachment 20 is of a diameter such that when traction is placed on the guide wire 16, the attachment cannot enter the sheath 14. Thus, retracting the wire 16 into the sheath 14 detaches the device 18 at the point of attachment 20. The coil is now free within the blood vessel and may be carried distally as an embolus or may remain fixed at the placement location. This will be a function of the coil design chosen, but the detachment mechanism permits observation of the intravascular behavior of the device prior to detachment.

Figure 3:
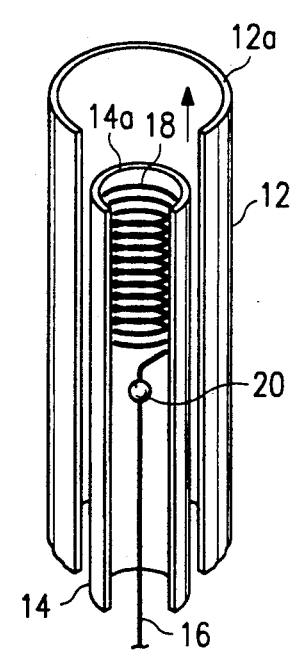
FIGS. 3, 4 and 5 illustrate a second method of detaching a jacketed endovascular device.
Figure 4:
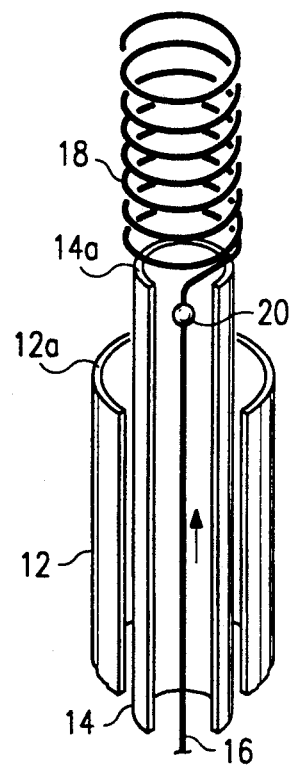
Figure 5:
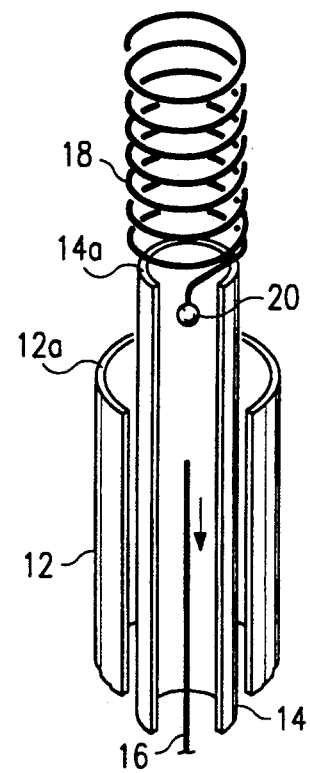

FIGS. 3, 4, and 5 illustrate a second method of detachment in which both the wire 16 and the endovascular device 18 are initially jacketed within the sheath 14. The device 18 can have both a compressed and an uncompressed state. While jacketed in the sheath 14, the device is in the compressed state. The sheath 14 is inserted into the catheter 12 until the distal end 14a of the sheath 14 is adjacent to the distal end 12a of the catheter 12. The guide wire 16 is then advanced within the sheath, thereby advancing the device 18 to a position distal to the sheath. Once unjacketed, the device 18 assumes an uncompressed state. In the uncompressed state, the device has a diameter greater than the sheath 14. Traction is then placed on the guide wire 16 bringing the device 18 into contact to the distal end 14a of the sheath 14. The retraction force applied to the wire 16 detaches the device from the wire. With either method, the detachment of the device 18 and subsequent removal of the sheath and guide wire do not require removal of the catheter. Therefore, the same catheter may be used to position additional devices if such are required.

Figure 6:
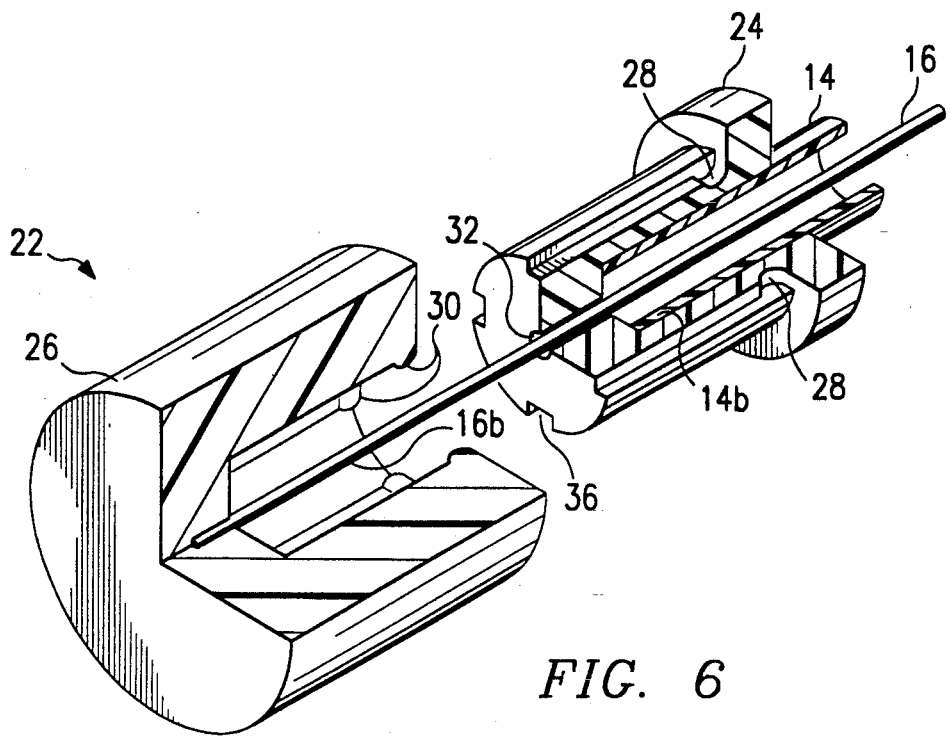
FIGS. 6 and 7 illustrate a hub design at the proximal (external) end of the system wherein both the sheath and guide wire are attached to respective hubs.
Figure 7:
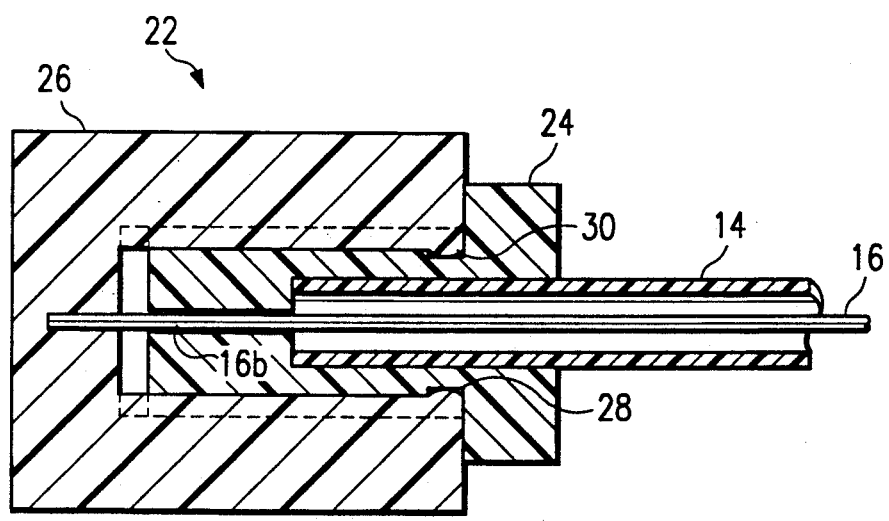

FIGS. 6 and 7 illustrate one embodiment of a hub assembly 22. The design of the hub assembly 22 can vary. However, the assembly generally comprises a sheath hub 24 removably attached to a wire hub 26. The proximal end 14b of the sheath 14 is rigidly attached to the sheath hub 24. Likewise, the proximal end 16b of the guide wire 16 is attached to the wire hub 26. A canal 32 exists through the sheath hub 24 which allows the guide wire 16 to pass freely to the wire hub 26. The wire hub 26 and sheath hub 24 can be interlocked such that accidental retraction of the guide wire 16 within the sheath 14 is prevented.

In use, the hubs are attached while the sheath is guided through the catheter. To detach an unjacketed device, the wire hub 26 is withdrawn from the sheath hub 24. To detach a jacketed device, the wire hub 26 is advanced relative to the sheath hub 24 until the device is unjacketed and then withdrawn relative to the sheath hub 24. This advancement motion would require modification of the sheath hub 24 to provide for a forward position. Movement should be substantially translational between the guide wire 16 and the sheath 14. Rotational movement should be minimized because it would produce unpredictable torque at points in the catheter 12. This would increase surface friction along the length of the catheter, increasing the likelihood of device failure by twisting and breakage of the guide wire. Axial grooves 36 minimize rotational movement.

Though many different designs may be utilized for the hub assembly 22, certain features must be shared by all in order to ensure safety of delivery without unintended detachment. First, the sheath 14 should be rigidly embedded or fused within the sheath hub 24. The bonding of the sheath within its hub ca be either mechanical or chemical. Failure of this attachment could lead to the retraction of the guide wire, wire hub and sheath hub, with the loss of control over the sheath within the catheter. Second, a channel 32 should exist through the sheath hub 24 which exceeds the diameter of the guide wire 16 permitting free movement of the guide wire 16 through the sheath hub 24. Third, the guide wire 16 should be rigidly embedded in the wire hub 26 such that it cannot inadvertently pull from the hub. It should be noted that unintentional breakage of the guide wire or its withdrawal from the hub would not necessarily result in inadvertent detachment of the endovascular device. Last, the wire hub 26 and sheath hub 24 must be interlocked or attached to each other in some fashion that is on the one hand rigid but on the other hand reversible. For instance, a locking band may be attached between the two hubs which can be removed at the time of detachment. Alternatively, thin plastic connections may be utilized such as are commercially currently used on milk cartons, or a twist-type unlocking mechanism may be employed. The locking mechanism shown in FIGS. 6 and 7 involves the interdigitations 28, 30 on the sides of the hubs.

The materials used for the elements of the coaxial traction detachment apparatus need not be limited. Currently, wires of stainless steel, platinum, tungsten, gold and other metals are used in medical applications. As discussed, several devices may be placed using the present detachment method. The most obvious of these are intravascular coils, produced currently by at least two manufacturers: Target Therapeutics of San Jose, Calif. and Cook, Inc. of Bloomington, Ind. Coils currently available from the above manufacturers are constructed of platinum and stainless steel alloys. Likewise, the attachment means can also involve different materials. Attachment of the guide wire 16 to the endovascular device 18 can be either by solid or mechanical means. Solid attachment can include the use of a solder, glue or by welding. Mechanical means can include intertwining fibers from a coil device with the guide wire such that their separation requires traction against the tip of the sheath. The sheath could be made of materials from relatively rigid stainless steel to relatively flexible teflon.

Factors to be considered in material choice can include the desired application and the strength of the delivery sheath used. For example, detachment of a larger device 18 into a large branch artery arising from the abdominal aorta may be achievable with a larger, sturdier system wherein the tensile strength is maximized. Larger coils can have a diameter of approximately 0.035" to 0.038". This would perhaps allow the use of a relatively large stainless steel sheath and stainless steel guide wire. The coil could be soldered to the guide wire with a lead-based solder. Significant traction could be placed on the guide wire 16 within the sheath 14 to achieve detachment without distortion of the sheath 14.

However, for placement of a smaller coil in a distal artery in the brain, the rigidity of the stainless steel sheath would not permit navigation of the tortuous vessels encountered during that catheterization. Thus, compromises may be necessitated including the use of more flexible synthetic materials for both the guide wire and the sheath. For example, the sheath could be made of a polyethylene or polytetrafluoroethylene (e.g. teflon). If a flexible sheath is used, a strong bond between the guide wire and device would necessitate strong traction to achieve detachment. This may result in partial collapse of a flexible sheath, causing some retraction of the device to an undesirable intravascular location. Thus, a weaker attachment between the guide wire 16 and the device 18 can be used. For example, a silicone based glue like adhesive could be used. In sum, the materials of the device, the guide wire, the sheath, and the mechanism of attachment must be chosen to match the anticipated application.

Additionally, modifications to the guide wire may include attachment of more flexible material to its distal end, enabling a more floppy distal device design. This modification would likely require modification of the solder or glue used to attach the embolic device, such that detachment would be achieved with more gentle traction. Moreover, with the advent of catheter technologies allowing distal vascular navigation, intraarterial chemotherapy for malignant brain tumors has become possible. It may be possible to deliver these or other drugs in biodegradable media to distal vascular sites using this type of system. In this instance, the "device" would be the nonmetallic biodegradable medium. The guide wire may be imbedded in the medium itself, rather than attached by glue or solder. In this instance, the guide wire would be mechanically detached from the medium by the traction of the medium against the sheath.

Utilization of the present coaxial traction detachment apparatus and method will most frequently occur via a transfemoral catheterization, either arterial or venous. A catheter, such as an angiographic catheter, will be placed such that its tip is near the desired detachment location. In some cases, this will involve a coaxial catheterization. For instance, in cerebral embolizations it is common to place a first catheter from the femoral approach into the carotid or vertebral artery. From there, a second smaller catheter is inserted by way of the angiographic catheter and advanced to a point within the brain near the pathology, and the embolization is conducted through this smaller catheter.

Following angiographic verification of placement of the smaller catheter, the device/sheath/guide wire will be introduced into the catheter. Following introduction, the device/sheath/guide wire combination are advanced within the catheter until the device can be seen under fluoroscopy to be exiting the catheter. When the device is observed to have exited the catheter completely and to lie in an appropriate position and configuration, the wire hub 26 is disconnected from the sheath hub 24. The wire hub 26 is then withdrawn while the sheath hub 24 is held in position, resulting in separation between the guide wire hub 26 and sheath hub 24. This action results in retraction of the guide wire 16 within the sheath 14. Since the device 18 diameter exceeds the inner diameter of the sheath, the device cannot retract into the sheath. This resistance to retraction takes place at the tip of the sheath, resulting in tension at that point between the guide wire and the device, producing detachment at that point. Once detachment takes place, the tension of the guide wire 16 within the sheath 14 is relieved and the guide wire 16 and sheath 14 can be withdrawn, leaving the deposited device 18 behind.

Although preferred embodiments of the invention have been described in the foregoing Detailed Description and illustrated in the accompanying drawings, it will be understood that the invention is not limited to the embodiments disclosed, but is capable of numerous rearrangements, modifications, and substitutions of parts and elements without departing from the spirit of the invention. Accordingly, the present invention is intended to encompass such rearrangements, modifications, and substitutions of parts and elements as fall within the scope of the invention.

What is claimed is:

1. A coaxial traction detachment apparatus for use with a catheter comprising:
   (a) a sheath within said catheter, said sheath having a proximal end and a distal end;
   (b) a guide wire within said sheath, said guide wire having a proximal end and a distal end;
   (c) an attachment between an endovascular device and the distal end of the guide wire, said attachment breakable by traction against the distal end of the sheath from retraction of the guide wire within the sheath;
   (d) a sheath hub attached to the proximal end of the sheath; and
   (e) a guide wire hub attached to the proximal end of the guide wire.

2. The coaxial traction detachment apparatus of claim 1 wherein said sheath hub and said guide wire hub are releasably locked to each other.

3. The coaxial traction detachment apparatus of claim 1 wherein said sheath is slidably disposed within said catheter.

4. The coaxial traction detachment apparatus of claim 1 wherein said guide wire is slidably disposed within said sheath.

5. The coaxial traction detachment apparatus of claim 1 wherein said attachment comprises solid means.

6. The coaxial traction detachment apparatus of claim 1 wherein said attachment comprises mechanical means.

7. The coaxial traction detachment apparatus of claim 1 wherein said endovascular device has a compressed state and an uncompressed state and wherein the endovascular device is jacketed within the sheath in the compressed state.

8. The coaxial traction detachment apparatus of claim 1 wherein said device is a coil.

9. A coaxial traction detachment apparatus comprising:
   (a) a catheter;
   (b) a sheath slidably disposed within said catheter, said sheath having a proximal end and a distal end;
   (c) a guide wire slidably disposed within said sheath, said guide wire having a proximal end and a distal end;
   (d) an attachment between an endovascular device and the distal end of the guide wire, said attachment breakable by traction against the distal end of the sheath from retraction of the guide wire within the sheath;
   (e) a sheath hub attached to the proximal end of the sheath; and (f) a guide wire hub attached to the proximal end of the guide wire wherein said guide wire is slidably disposed within said sheath.

10. The coaxial traction detachment apparatus of claim 9 wherein said sheath hub and said guide wire hub are releasably locked to each other.

11. The coaxial traction detachment apparatus of claim 9 wherein said sheath is slidably disposed within said catheter.

12. The coaxial traction detachment apparatus of claim 9 wherein said attachment comprises solid means.

13. The coaxial traction detachment apparatus of claim 9 wherein said attachment comprises mechanical means.

14. The coaxial traction detachment apparatus of claim 9 wherein said endovascular device has a compressed state and an uncompressed state and wherein the endovascular device is jacketed within the sheath in the compressed state.

15. The coaxial traction detachment device of claim 9 wherein said device is a coil.

16. A method of detaching a device attached to the distal end of a guide wire, only said guide wire within a sheath, and said sheath, guide wire and device within a catheter, said method comprising:

(a) positioning the distal end of the catheter adjacent to a device detachment location;
(b) advancing the sheath and device beyond the distal end of the catheter;
(c) retracting the guide wire to bring the device against the distal end of the sheath; and
(d) applying a predetermined force to the guide wire to detach the device from the guide wire.

17. A method of detaching a device attached to the distal end of a guide wire, said guide wire and said device within a sheath, said device having a compressed and an uncompressed state, and said sheath, guide wire, and device within a catheter, said method comprising:

(a) positioning the distal end of the catheter adjacent to a device detachment location:
(b) advancing the sheath beyond the distal end of the catheter;
(c) advancing the guide wire and attached device beyond the distal end of the sheath, allowing the device to assume its uncompressed position;
(d) retracting the guide wire to bring the device against the distal end of the sheath; and
(e) applying a predetermined force to the guide wire to detach the device from the guide wire.

* * * * *

UNITED STATES PATENT AND TRADEMARK OFFICE
CERTIFICATE OF CORRECTION

PATENT NO. : 5,263,964
DATED : November 23, 1993
INVENTOR(S) : Phillip D. Purdy

It is certified that error appears in the above-indentified patent and that said Letters Patent is hereby corrected as shown below:

Col. 1, line 48 , "ca" should be --can--.

Col. 3, line 47, "o" should be --of--.

Col. 6, line 11, "ca" should be --can--.

Signed and Sealed this

Twenty-sixth Day of April, 1994

Attest:

BRUCE LEHMAN

Attesting Officer     Commissioner of Patents and Trademarks